United States Patent
Abraham et al.

(10) Patent No.: US 7,151,817 B1
(45) Date of Patent: Dec. 19, 2006

(54) X-RAY INSPECTION SYSTEMS WITH IMPROVED RADIATION ATTENUATION SHIELDING

(75) Inventors: Douglas Q. Abraham, Topsfield, MA (US); Eric N. Finck, Newton, MA (US); David Schafer, Rowley, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 11/224,567

(22) Filed: Sep. 12, 2005

(51) Int. Cl.
*G01N 23/04* (2006.01)

(52) U.S. Cl. .................. 378/57; 378/208

(58) Field of Classification Search ............ 378/57, 378/4, 208, 20; 250/515.1, 482.1, 497.1
See application file for complete search history.

(56) References Cited

U.S. PATENT DOCUMENTS 6,058,159 A * 5/2000 Conway et al. ............ 378/68

2005/0185757 A1 * 8/2005 Kresse et al. ............ 378/57
2005/0213713 A1 * 9/2005 Cadwalader et al. ........ 378/203

* cited by examiner

*Primary Examiner*—Edward J. Glick
*Assistant Examiner*—Hoon Song
(74) *Attorney, Agent, or Firm*—McDermott Will & Emery LLP (57) ABSTRACT

Arrangements of X-ray inspection systems are described. An X-ray inspection system may include a shielded housing with a tunnel passageway and entrance and exit ports. The system may include an X-ray inspection station defining a rectilinear coordinate system, an X-ray source, and a detection system for generating images of articles that are located in the inspection station. A conveyor assembly may be included. A plurality of flexible X-ray attenuating, spaced-apart, hanging strips may be distributed within the shielded housing between the ports and across the entire tunnel passageway. The X-ray inspection system may include at least one curtain of flexible X-ray attenuating hanging strips. Each curtain may include a plurality of sets of contiguous strips, the strips of each set being of equal length and distributed across the tunnel passageway. The strips of at least one set are shorter than the strips of at least one other set.

9 Claims, 8 Drawing Sheets

X-RAY INSPECTION SYSTEMS WITH IMPROVED RADIATION ATTENUATION SHIELDING

BACKGROUND

The U.S. Transportation Security Administration (TSA) and other similar agencies throughout the world are responsible for identifying dangerous devices and/or contraband within passenger baggage brought onboard public transportation systems. Various X-ray baggage scanning systems are known for detecting the presence of such materials, e.g., explosives and other prohibited items, in baggage or luggage prior to loading the baggage onto commercial carriers, e.g., a commercial aircraft. Since many explosive materials may be characterized by a range of densities differentiable from that of other items typically found in baggage, explosives are generally amenable to detection by X-ray equipment. A common technique of measuring the density of a material is to expose the material to X-rays and to measure the amount of attenuation, and therefore radiation absorbed by the material, the absorption being dependent on the density and atomic number of the material.

Many X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates a stationary X-ray beam that passes through and is partially attenuated by the baggage, as the baggage is moved into and positioned within the beam, before being received by the detector array. During each measuring interval, each detector of the detector array generates data representative of the integral of the density of the segment of the baggage through which the detected portion of the X-ray beam passes. The data acquired by the detector array during each measuring interval is used to form one or more raster lines of a two dimensional image. As the conveyor belt transports the baggage past the stationary source and detector array, the scanner generates a two dimensional image closely related to the areal density of the baggage, as viewed by the stationary detector array. The image is typically displayed for analysis by a human operator.

Recently developed baggage scanners have employed X-ray computed tomography (CT) to improve the image by eliminating the line integral and producing images that have pixel values related to physical density instead of areal density. These CT scanner images are then used to identify objects within baggage positioned in the scanner. Representative examples include the AN6400 EXACT system manufactured by the current assignee and the Invision CTX 9000® system manufactured by GE Invision, Inc. Such systems typically include a CT scanner that includes an X-ray source and an X-ray detector system secured to diametrically opposite sides of an annular-shaped platform or disk. The disk is rotatably mounted within a supporting frame, or gantry support, so that in operation the disk can rotate while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. The X-ray source typically generates a fan-shaped beam, or "fan" beam, of X-rays that passes through a planar imaging field, and is received by the detectors. More advanced CT scanners include an array of detectors, arranged in multiple rows, which are simultaneously irradiated by an X-ray source "cone" beam so that data relating to multiple slices can be simultaneously acquired.

CT scanners are typically characterized by a rectilinear coordinate system, e.g., one defined by X-, Y- and Z-axes, in which the axes intersect and are all normal to one another at the center of rotation of the disk during its operational motion. This center of rotation is commonly referred to as the "isocenter." The Z-axis is defined by the rotation axis and the X- and Y-axes are defined by and lie within the imaging field. The fan and cone beams are thus each defined as the volume of space defined between the X-ray source and the receiving surfaces of the detectors of the detector array that are exposed to the X-ray beam emanating from the source. Each detector generates an output signal representative of the intensity of the X-rays incident on that detector.

As the disk rotates around the object being scanned, the scanner generates a plurality of projections at a corresponding plurality of projection angles. Since the X-rays are partially attenuated by all the mass in their path, the output signal generated by each detector is representative of the density of the portion of any object disposed in the imaging field and in the projection direction between the X-ray source and that detector.

A CT image of the object may be generated from all the projection data collected at each of the projection angles by using appropriate reconstruction software and algorithms. In a multi-slice scanner the CT images are representative of the density of a plurality of two dimensional "slices" of the object through which the cone beam has passed during the rotation of the disk through the various projection angles. The data from multiple slices can be used to reconstruct and display three dimensional images of the scanned object.

Further, the CT type baggage scanners use a conveyor system including a conveyor belt to move objects into the scanner one object at a time. In the reference Invision machine the conveyor stops when an object is positioned in the scanner, and a constant axis CT scan (with no movement in the Z-axis direction) is performed on the object. In order to increase throughput, the AN6400 EXACT baggage scanner is designed to move the objects continuously through the CT scanner while helical scans (where there is movement in the Z-axis direction during a scan) are performed.

Since X-rays can be harmful, shielding of some sort is typically used with X-ray scanners to protect people in proximity to the scanners. Government regulations may require such shielding to reduce detectable levels of radiation outside of the scanners to certain levels. Often high density materials such as lead or bismuth are used to provide such shielding. In the Invision scanner, for example, doors of shielding material are provided above the conveyor at the entrance and exit ports of the scanner. The doors are designed to open sequentially when objects are conveyed on the conveyor belt in and out of the scanner, so that whenever x-rays are on, at least one door on each side of the x-ray beam is closed. In the AN6400 EXACT scanner curtains of flexible strips of X-ray absorbent materials are provided at the entrance and exit ports of the scanner so as to provide shielding since the belt continuously moves even when scans are being performed.

For X-ray inspection systems that use such movable shield doors, the shields doors have presented problems including frequent break downs due to the complexity of the associated door movement mechanisms. This can have a negative impact on the throughput of articles passing through the related X-ray inspection systems, something that is undesirable for busy public transportation systems such as international airports.

Curtains with hanging strips of high-X-ray absorption fabric such as provided on the AN6400 EXACT scanner, allow for higher throughputs when used with a continuous running conveyor and a helical CT scanning inspection station. Such curtains each typically include a row of strips aligned side-by-side (contiguous with one another) across the width of the tunnel. The strips hang in the same vertical plane within the tunnel, most often just above or in contact with an associated conveyor belt. The strips are able to bend and flex to a degree to allow passage of articles through the tunnel by the conveyor system. These types of shield curtains are typically located at the entrance and exit ports of a containment tunnel. The curtains may also be located at one or more locations along the tunnel between the entrance and exit ports to provide improved shielding since at any one time, the strips of one or more curtains may be displaced by a moving bag.

Such prior art curtains may be effective when used with a continuously operating X-ray source and when overall article throughput is low and the total radiation in the tunnel is limited by either low x-ray beam current or high degree of x-ray collimation. Despite this, the use of such prior art curtains still present certain problems. For example, when the collimated X-ray beam is expanded beyond a certain size, or when the flux within a system is increased above a certain level, the radiation that escapes through the curtains at the ports as the strips are displaced by objects passing through can increase above acceptable levels. Because the X-ray source is continually operating, unacceptable radiation levels can escape unimpeded from a tunnel when the strips in such curtains are displaced by a moving bag. Additionally, because the individual strips of such curtains tend to curl about the vertical axis as they are used over a period of time, the effectiveness of these types of curtains can degrade to an unacceptable degree over time.

Utilizing thicker curtains may not be a viable solution under all circumstances. Increasing the thickness of the fabric decreases the flexibility of the curtain materials. As a result, the strips of the curtains are less able to be displaced and/or bend when contacted by articles to be inspected. The articles can consequently experience increased resistance against movement within the inspection system. This can cause articles to jam in the inspection system, compromising its effectiveness.

It would be beneficial, therefore, for providing adequate radiation attenuation shielding that allows for use of increased X-ray fluxes and beam diameters in X-ray inspection systems, whether continuously or intermittently operating, while achieving given radiation levels outside of the systems. At the same time, it would be beneficial for radiation attenuation shielding that allows X-rays inspection systems to better accommodate increased volumes or throughput of articles such as passenger baggage. It would also be beneficial for the radiation attenuation shielding to accommodate a wide range of sizes of articles such as those of common passenger baggage.

SUMMARY

The present disclosure is generally directed to apparatus for radiation attenuation that overcome problems noted for the prior art. The radiation attenuation apparatus are suitable for use in X-ray inspection systems, such as those use to screen passenger baggage at airports.

One arrangement of the present disclosure may include an X-ray inspection system for inspecting articles. The X-ray inspection system may include a shielded housing including entrance and exit ports so as to define a tunnel passageway between the entrance and exit ports, and an X-ray inspection station (a) defining a X-, Y- and Z-axis coordinate system, (b) disposed between the entrance and exit ports and (c) including a source of X-rays and a detection system for generating X-ray images of the articles when each is located in the inspection station, wherein the X-rays emanate from a plurality of loci during operation of the X-ray inspection station. The system may also include a conveyor assembly for conveying articles to and from the X-ray inspection station through the tunnel passageway along the Z-axis of the coordinate system through the entrance and exit ports. A plurality of flexible X-ray attenuating, spaced-apart, hanging strips may be included and may be distributed within the shielded housing between the X-ray inspection station and each of the entrance and exit ports across the entire tunnel passageway, wherein the spaced-apart strips are distributed so as to provide uniform attenuation of X-rays emanating from each of said loci toward the entrance and exit ports so as to minimize leakage radiation through the entrance and exit ports while allowing each article to displace strips as it passes through the shielded housing.

The X-ray inspection station may include a computed tomography (CT) system including the source of X-rays and the detection system. The CT system may perform multi-slice scans of each of the articles when the articles are located in the inspection station. The conveyor system may continuously transport articles through the inspection system so that the CT system performs multi-slice helical scans.

The X-ray inspection system may further include at least one curtain of flexible X-ray attenuating hanging strips between the inspection station and each of the entrance and exit ports. The hanging strips of each curtain are distributed contiguous with one another substantially in a plane substantially normal to the Z-axis so as to provide uniform attenuation of X-rays emanating from within the inspection station, and allowing articles to displace strips as each article comes in contact with one or more of the hanging strips of the curtain as the article passes through the shielded housing by the conveyor system, wherein the plurality of flexible X-ray attenuating, spaced-apart, hanging strips are disposed between each of the curtains and the inspection station.

Each curtain may include a plurality of sets of contiguous strips, the strips constituting each set being of equal length and distributed across the tunnel passageway, and the strips of at least one set are shorter than the strips of at least one other set. The set of shorter strips may be positioned in front of the set of longer strips (in the direction from which conveyed articles move) and terminate at a higher position than the longer strips so that articles smaller than a predetermined height passing through the curtain will displace the longer strips without displacing the shorter strips.

Another arrangement may include an X-ray inspection system for inspecting articles, comprising a shielded housing including entrance and exit ports so as to define a tunnel passageway between the entrance and exit ports, and an X-ray inspection station (a) defining a X-, Y-, and Z-axis coordinate system, (b) disposed between the entrance and exit ports and (c) including an X-ray source and a detection system for generating data representing X-ray images of the articles when each is located in the inspection station. A conveyor assembly may be present for conveying articles to and from the X-ray inspection station through the tunnel passageway along the Z-axis of the coordinate system through the entrance and exit ports. The system may also include at least one curtain of flexible, X-ray attenuating strips disposed between the inspection station and each of the entrance and exit ports, and distributed contiguous with one another substantially in a plane substantially normal to the Z-axis so as (a) to provide uniform attenuation of X-rays emanating from within the inspection station, and (b) allow articles to pass through the curtains as they pass through the shielded housing. Each curtain includes strips of different lengths such that the strips of the curtain displaced as an article moves through the curtain by the conveyor assembly is a function of the size of the article.

Each curtain may include a plurality of sets of contiguous strips, the strips of each set being of equal length and distributed across the tunnel passageway, and the strips of at least one set are shorter than the strips of at least one other set. The set of shorter strips may be positioned in front of the set of longer strips and terminate at a higher position than the longer strips so that articles smaller than a predetermined height passing through the curtain will displace the longer strips without displacing the shorter strips so as to improve the shielding capabilities of the curtain when in use.

BRIEF DESCRIPTION OF THE DRAWINGS

Various aspects of the disclosure itself may be more fully understood from the following description when read together with the accompanying drawings. The drawings are not necessarily to scale, emphasis instead being placed on the principles of the disclosure. In the drawings.

DETAILED DESCRIPTION

The present disclosure provides apparatus that overcome the problems associated with radiation shielding used in the prior art. Aspects of the present disclosure are directed to the use of bendable strips of relatively high density material in desired arrangements to attenuate X-ray radiation produced by X-ray inspection systems used for inspecting portable articles such as passenger baggage at the entrance and exit ports of the systems.

Figure 1:
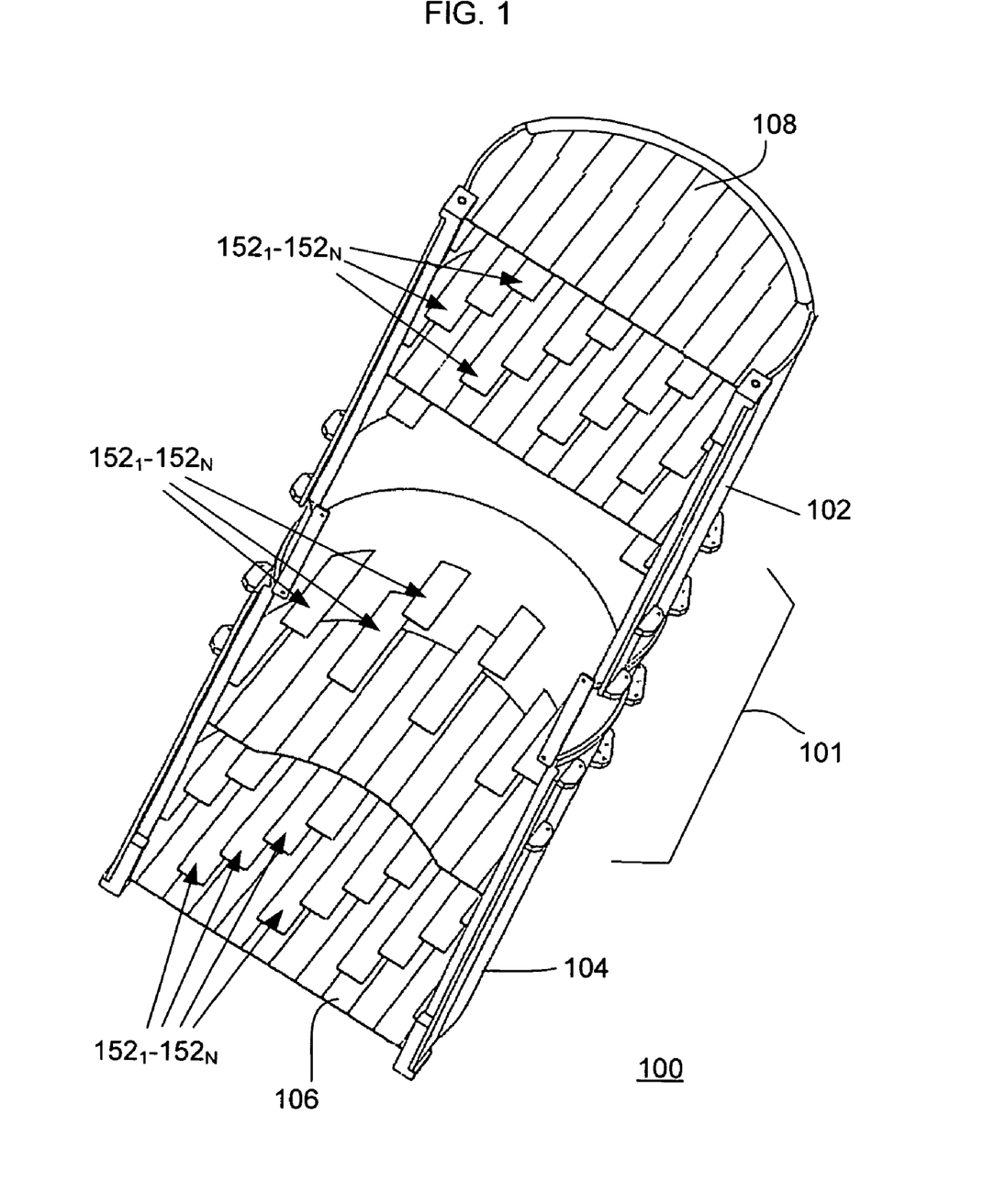
FIG. 1 shows a perspective view of the underside of a containment tunnel with multiple shield strips for use in an X-ray inspection system, according to one arrangement of the disclosure.

Referring to FIG. 1, a perspective view is shown of one arrangement 100 of the present disclosure including an underside of a containment tunnel 101 with two sections 102, 104. Multiple shield strips $152_1$–$152_N$ are arranged in a distributed manner along the length and across the width of the tunnel 101. Also shown are two shield curtains 106, 108, respectively located at entrance and exit ports to the tunnel 101. The tunnel 101 includes a middle portion to which a computed tomography (CT) scanner may be adapted and used as an inspection station, as described in further detail below for FIGS. 2–3. The tunnel 101 and shield strips $152_1$–$152_N$ are suitable for use in X-ray inspection systems, such as those employed to screen luggage and carry-on baggage for dangerous and banned items.

The shield strips $152_1$–$152_N$ may be made of suitable X-ray absorption materials that have sufficient flexibility and density. Examples of suitable materials for the shield strips $152_1$–$152_N$ include vinyl or cloth impregnated with high-density materials, such as lead or bismuth.

Figure 2:
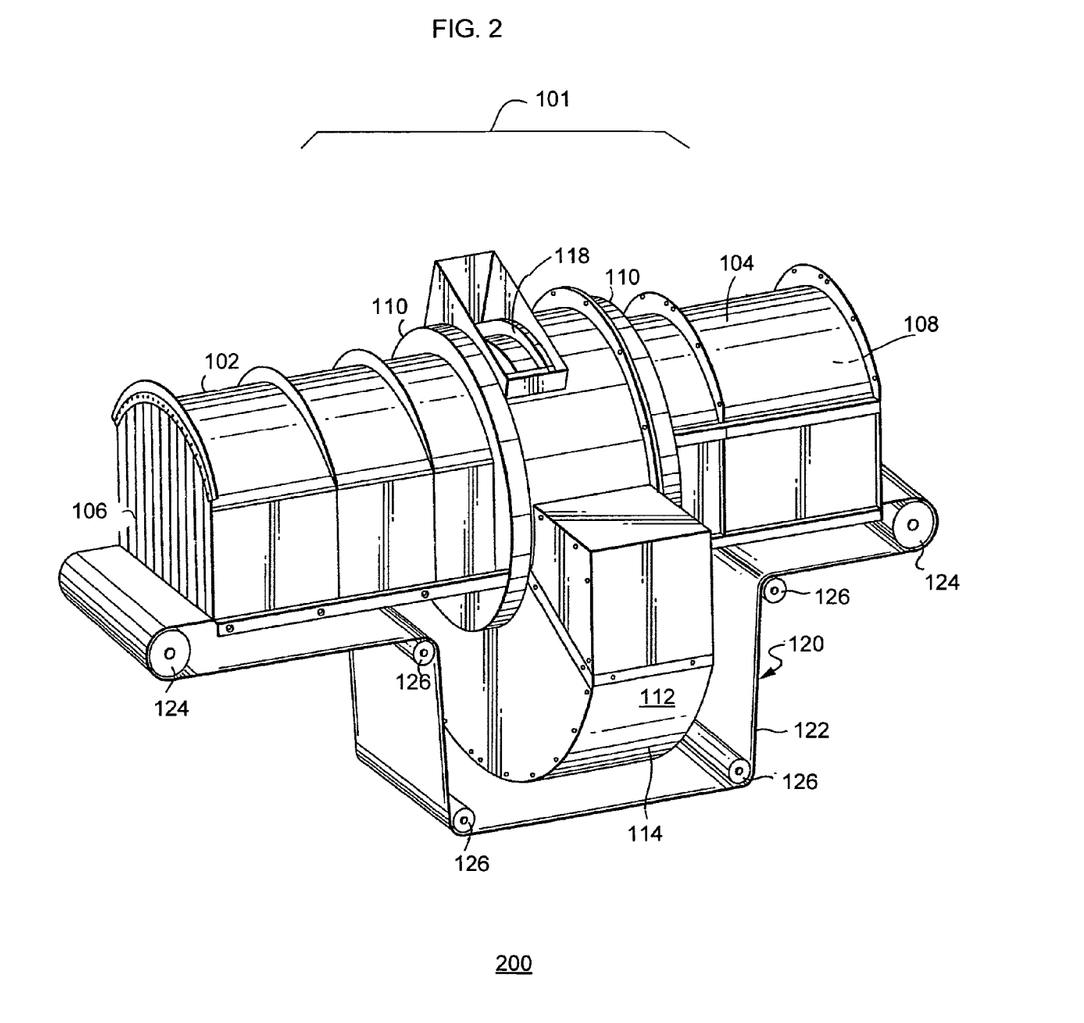
FIG. 2 shows a perspective view of an X-ray inspection system for inspecting articles, shown with an outer housing and internal support structures removed, to reveal a conveyor system and a rotatable X-ray containment shield, according to an arrangement of the present disclosure.

FIG. 2 is a perspective view of an exemplary arrangement of the present disclosure including an X-ray inspection system 200 for inspecting articles such as passenger baggage. System 200 is shown with an outer housing and internal support structures removed. The system 200 includes a tunnel 101 with two sections 102, 104 and entrance and exit ports 106, 108. A rotatable annular main body (shown as 136 in FIG. 3) and an X-ray containment shield 112 for enclosing a CT scanning system provides the middle portion of the tunnel 101. The rotatable containment shield 112 surrounds the annular platform to which an X-ray source and X-ray detector array are attached. The X-ray source is arranged to emit X-rays to articles located within the annular main body. The rotatable containment shield 112 is attached to and supported by rings 110 that connect to respective tunnel sections 102, 104. The containment shield 112 may include an X-ray source housing (shown at 130 in FIG. 3) for housing a source of X-rays, and detector housing 114 for housing the detector array and electronics of acquiring the scanned data. The containment shield and inner platform are design to rotate about a rotation axis defining the Z-axis of the inspection system. A conveyor system 120 may be used to move articles into, through and out of the tunnel 101. The conveyor system 120 may include a conveyor belt 122 that passes through the tunnel 101 and around main pulleys 124 and idler pulleys 126.

In operation, the X-ray source generates a cone beam of X-rays that passes through a three dimensional imaging field. Articles to be scanned are moved through the imaging field of the inspection station, e.g., by the conveyor system. The cone beam is attenuated by the article as a function of density and then received by the detector array. The detector array in turn generates signals representative of physical attributes of portions of the baggage between the focal spot and the respective detector during the measuring interval. A plurality of projections are generated at a corresponding plurality of projection angles as the annular platform 112 rotates about the Z-axis. In a well known manner, signals from the detector array can be initially acquired by a data acquisition system, and subsequently processed by a computer for computed tomography (CT) reconstruction of the scanned article(s). In one exemplary embodiment, the X-ray source is a dual energy, helical-cone-beam, multi-slice CT system that provides a complete set of CT images of an entire three-dimensional object as it is scanned, and the X-ray detector is a high efficiency, wide dynamic range, solid-state, two dimensional X-ray detector array.

Figure 3:
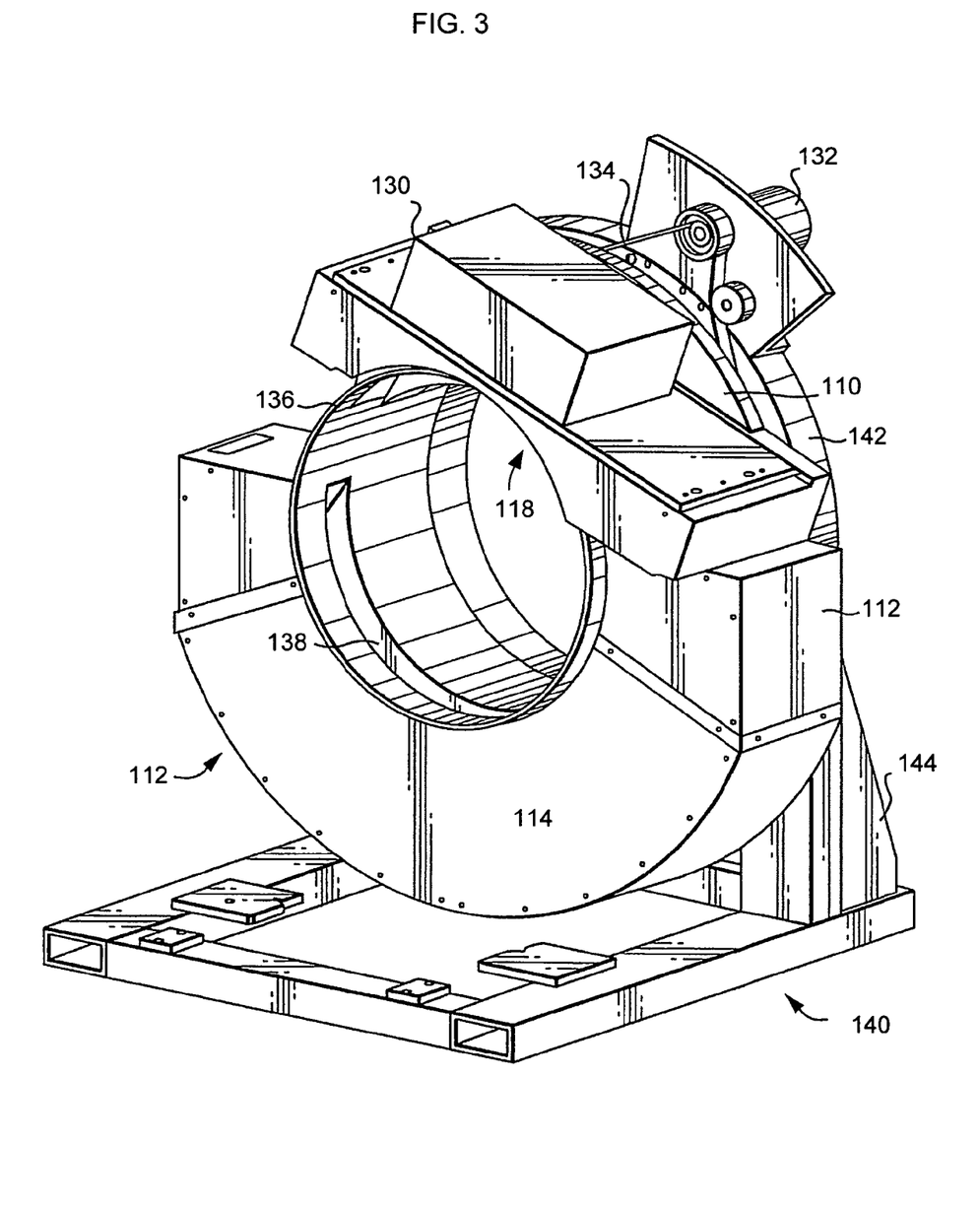
FIG. 3 shows a perspective view of the CT scanner for use at the inspection station of the X-ray inspection system of FIG. 2, with related supporting structure.

FIG. 3 shows is a perspective view of the rotatable X-ray containment shield of FIG. 2 with a gantry support structure 140 on which the X-ray containment shield 112 is supported for rotation. The gantry support structure 140 includes a stand 144 supporting an outer, non-rotating support ring 142, and an inner rotatable component ring 110 supported for rotation with respect to the support ring 142. A motor 132 is mounted on the support ring 142 and operatively connected to the component ring 110 through a pulley belt 134 received in an outer circumferential groove of the component ring 110. Although not shown, the component ring 110 is rotatably supported on the support ring through a bearing system. U.S. Pat. Nos. 5,982,844, 6,188,743 and 6,337,894, each of which is incorporated herein by reference, which are owned by the present assignee, and incorporated in their entirety by reference, provide examples of suitable gantry bearing systems and gantry drive pulley systems.

Figure 4:
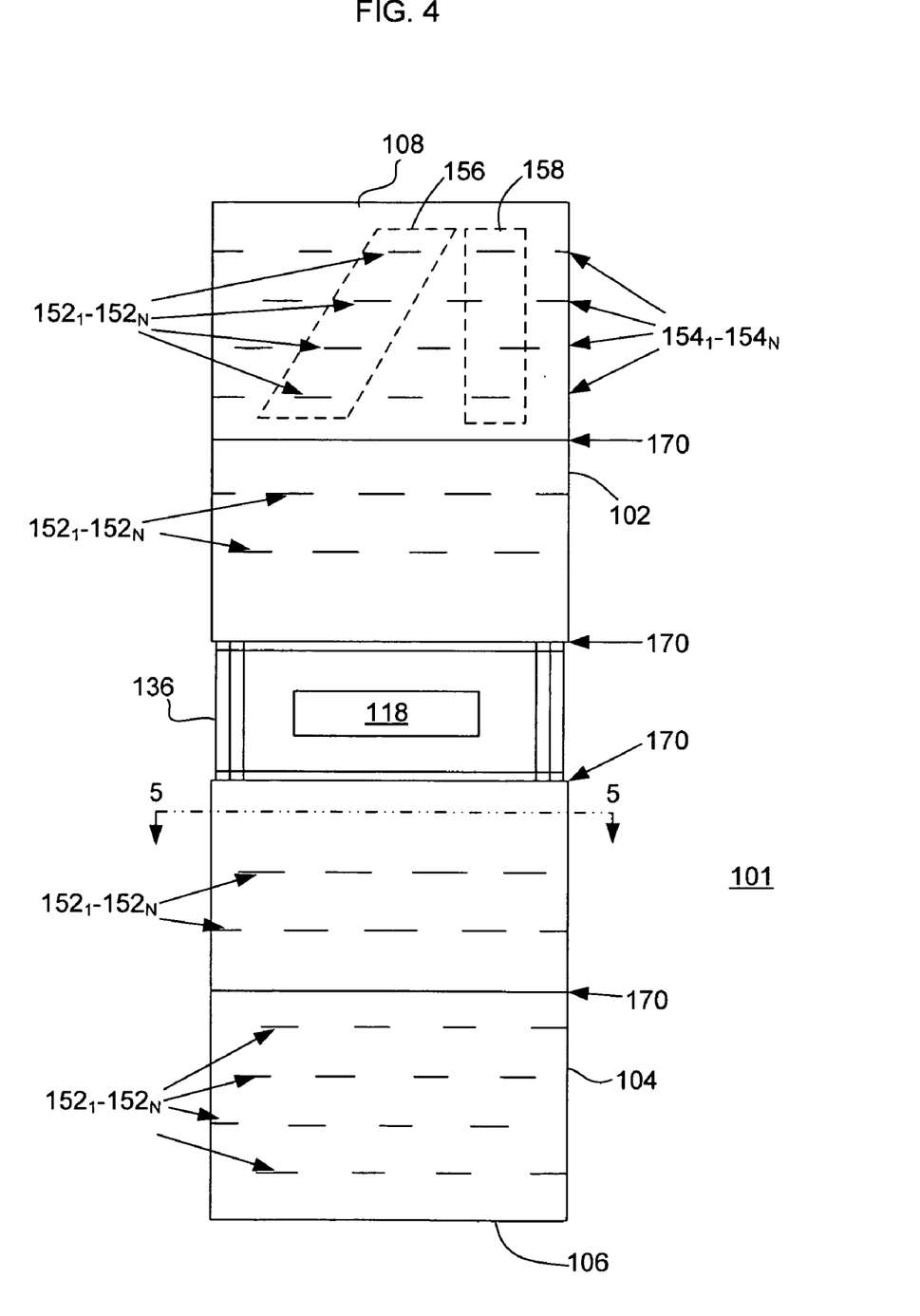
FIG. 4 shows a bottom view of the inspection tunnel including shield strips of FIG. 1.

FIG. 4 shows a bottom view of the tunnel 101 and shield strips $152_1$–$152_N$ of FIG. 1. The shielding strips $152_1$–$152_N$ are distributed in spaced apart, non-contiguous relation (as distinguished from the curtains) within the sections 102 and 104 of the tunnel 101 in such a way that for each section, 102, the strips $152_1$–$152_N$ provide uniform attenuation of any radiation emitted from any locus within the inspection station toward either the entrance or exit ports. As shown, the strips of adjacent rows $154_1$–$154_N$ are offset from one another as shown by dashed box 156, although other arrangements can be provided. One or more subsidiary curtains 170 may be present for certain applications.

This arrangement of the strips $152_1$–$152_N$ allows the entire area outside the entrance and exit ports to be properly shielded from radiation being emitted from within the inspection station. With the CT system operating continuously, the shielding effect provided by such an arrangement is redundant along the main axis (parallel or coaxial with the Z-axis of the scanner) of the tunnel sections, as shown by dashed box 158, with no open path available for radiation to travel in directions parallel to the axis from the inspection station to the entrance and exit ports even when one or more objects are displacing the shield strips $152_1$–$152_N$ in the tunnel 101. In this way, shielding sufficient to meet a desired radiation level outside the tunnel 101 may be obtained, without the use of overly thick and inflexible materials.

Figure 5:
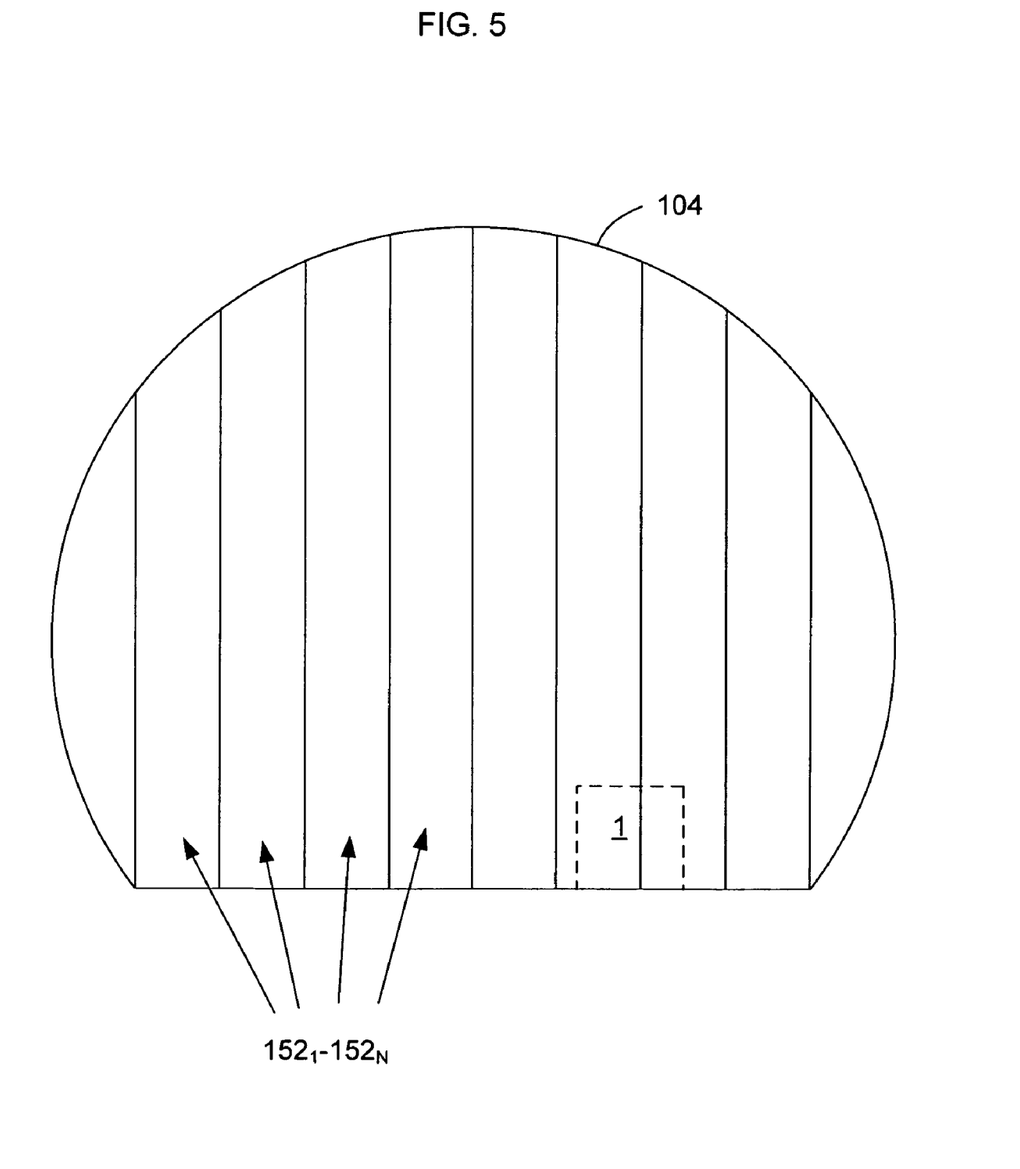
FIG. 5 shows a section view of the tunnel of FIG. 4 along cutting plane 5—5.

FIG. 5 shows a section view of the tunnel of FIG. 4 in a direction normal to cutting plane 5—5. As can be seen, projecting from any locus of from within the inspection station, the configuration of shield strips $152_1$–$152_N$ across the tunnel section 104 is continuous with no gaps between strips. Thus, additional shielding to X-ray radiation propagating along the tunnel is provided across the entire width of the tunnel section 104. This complete coverage occurs even when articles, e.g., luggage bag 1, are move through the tunnel 101, and bending or displacing of only one or few of the individual shield strips occurs.

Figure 6:
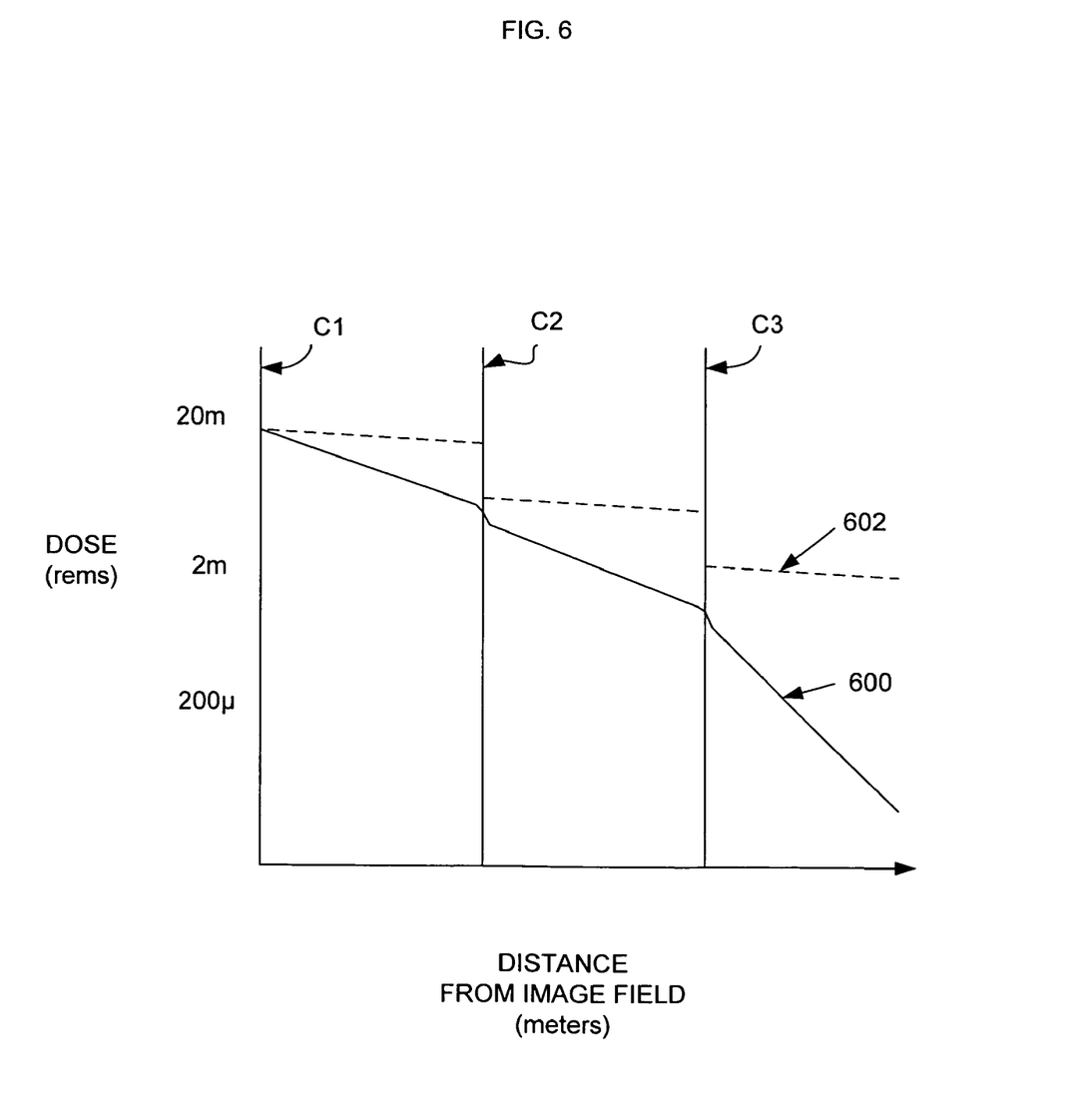
FIG. 6 is a graph showing a reduction in emitted stray radiation at the entrance and exit ports from use of arrangements of the present disclosure relative to prior art shielding techniques.

FIG. 6 is a graph showing an example of a reduction in measurable radiation within and emanating from an X-ray inspection system employing the arrangement of the present disclosure described in connection with FIGS. 1–5, relative to prior art shielding techniques. The relative distance from a representative X-ray inspection system is indicated, along with relative locations of curtains C1–C3. As can be seen, using only curtains results in stepped attenuation of the radiation 602, with attenuation occurring only at the curtain positions. In contrast, when the distributed strips 152 are used, e.g., the configuration as shown in FIG. 4, radiation levels 600 within the X-ray scanning system decrease more significantly as shown by the slope of 600.

FIG. 6 shows that using a dispersed distribution of shield strips can allow a certain level of radiation attenuation to be met over a shorter distance containment tunnel than is possible for the prior art. Additionally, for a given length of containment tunnel, a greater degree of X-ray attenuation can be achieved.

Figure 7:
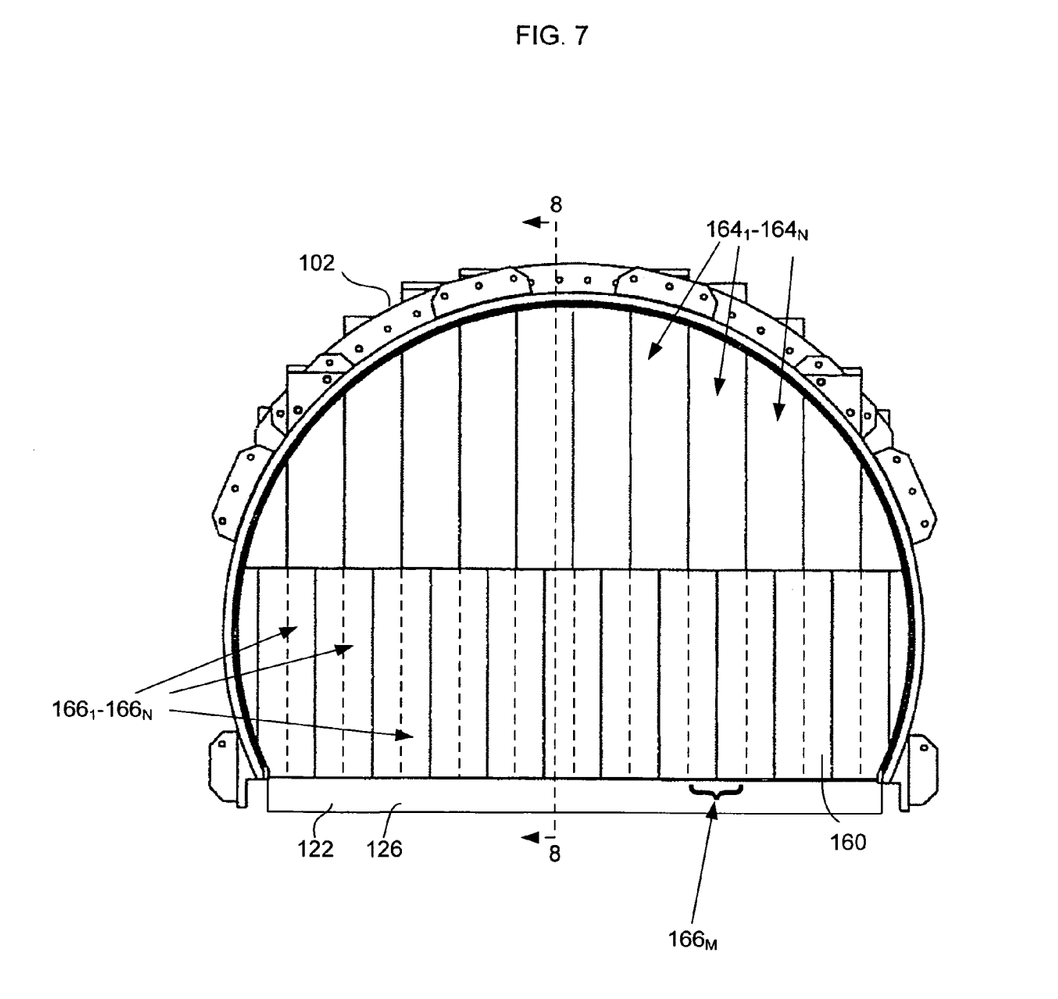
FIG. 7 shows an end view of a multi-level curtain according to one arrangement of the present disclosure.
Figure 8:
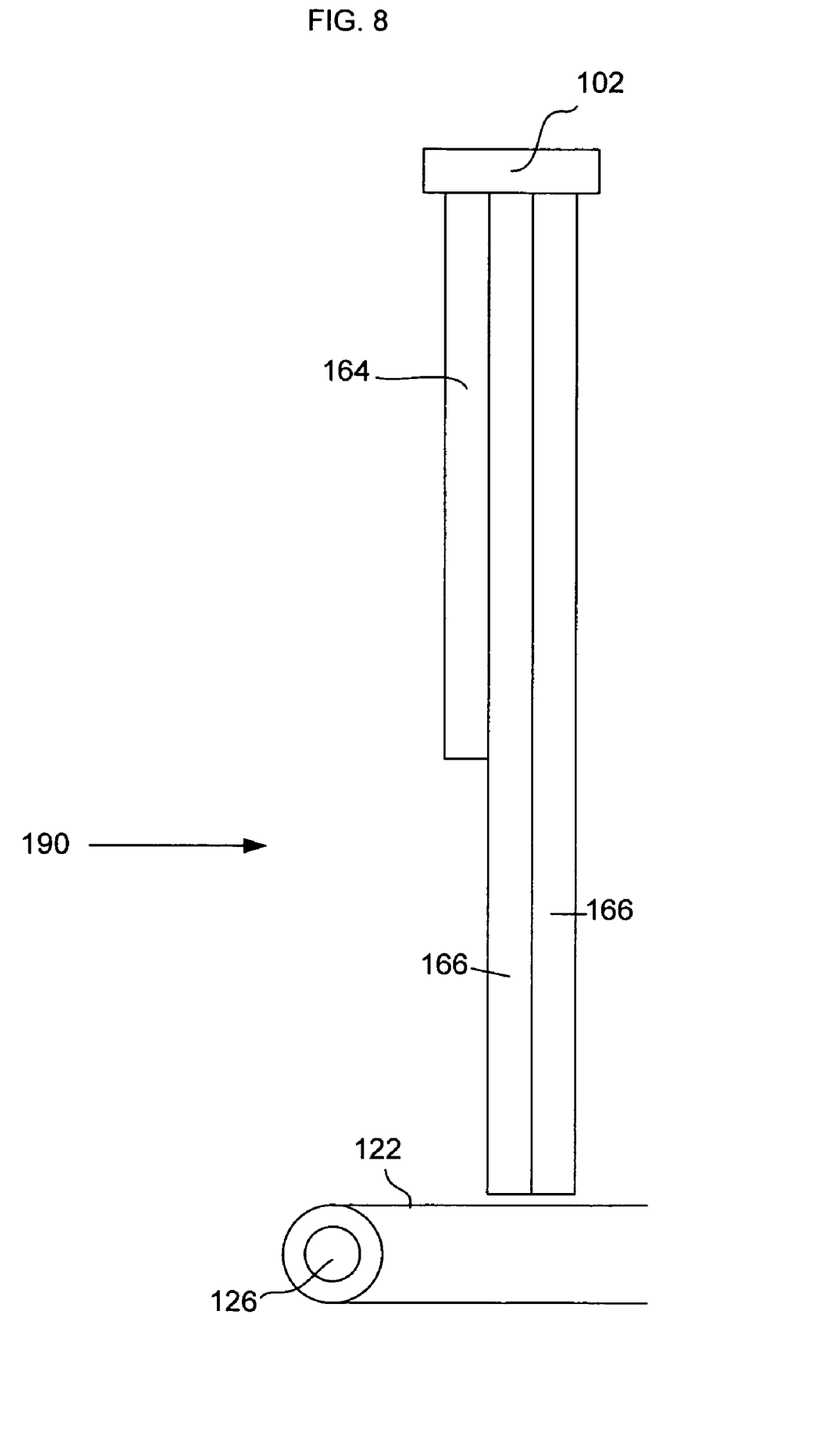
FIG. 8 shows a cross sectional view through a multi-level curtain of the type shown in FIG. 7.

FIGS. 7 and 8 show a multi-layer curtain 160 according to another arrangement of the present disclosure. The curtain includes strips of flexible, X-ray attenuating shield strips. The curtain 160 includes multiple sets or layers of contiguous strips $164_1$–$164_N$ and $166_1$–$166_N$. The strips of any particular set or layer are of equal length and are distributed across the entire width of tunnel passageway. The length of the strips of each set can differ from set to set, with the shorter sets of strips positioned in front of (facing the on-coming direction of the conveyed objects on the conveyor) so that less resistance is offered to smaller articles passing through the associated X-ray inspection system. In addition to being arranged in a contiguous manner, at least two sets or layers of the longest strips may also overlap in the horizontal direction as shown by $166_M$ to facilitate optimal shielding. While three sets or layers of strips are shown (one short and two long), more than three may be employed for some applications. For example, multiple sets or layers of curtains may be used, with the lengths of the different sets or layers being determined by the variation in the anticipated sizes objects to be inspected.

With this arrangement, the set or layer of shorter strips are preferably positioned in front of the set of longer strips, relative to direction of article movement, and terminate at a higher position than the longer strips so that articles smaller than a predetermined height passing through the curtain will displace the longer strips without displacing the shorter strips. Since the shorter strips are not displaced they continue to provide optimum protective shielding from radiation emitted from within the inspection station through that portion of the curtain.

Accordingly, arrangements of present disclosure offer advantages over the prior art. Shielding strips may be located within an X-ray inspection system to reduce the radiation that can leave the system through the entrance and exit ports. Such arrangements allow a continuous conveyance of varying sized objects that are passing through an X-ray inspection system while attenuating radiation to desired levels. Greater amounts of shielding and radiation attenuation may be realized for a given length of containment tunnel. The distributed strips provide a given amount of attenuation, with less resistance to articles passing through the inspection system. Additionally, higher power and flux X-ray sources may be used while still meeting required radiation emission and exposure standards. X-ray inspection systems using radiation attenuation apparatus according to certain arrangements may accommodate a wide range of sizes of articles such as those of common passenger baggage.

The disclosure may be embodied in other specific forms without departing from the spirit or essential characteristics thereof. The present arrangements are therefore to be considered in respects as illustrative and not restrictive, the scope of the disclosure being indicated by the appended claims rather than by the foregoing description, and all changes that come within the meaning and range of the equivalency of the claims are therefore intended to be embraced therein.

The invention claimed is:

1. An X-ray inspection system for inspecting articles, comprising:
   a shielded housing including entrance and exit ports so as to define a tunnel passageway between the entrance and exit ports, and an X-ray inspection station (a) defining a X-, Y- and Z-axis coordinate system, (b) disposed between the entrance and exit ports and (c) including a source of X-rays and a detection system for generating X-ray images of the articles when each is located in the inspection station, wherein the X-rays emanate from a plurality of loci during operation of the X-ray inspection station;

a conveyor assembly for conveying articles to and from the X-ray inspection station through the tunnel passageway along the Z-axis of the coordinate system through the entrance and exit ports; and a plurality of flexible, X-ray attenuating, spaced-apart, hanging strips distributed within the shielded housing between the X-ray inspection station and each of the entrance and exit ports across the entire tunnel passageway, wherein the spaced-apart strips are distributed so as to provide uniform attenuation of X-rays emanating from each of said loci toward the entrance and exit ports so as to minimize leakage radiation through the entrance and exit ports while allowing each article to displace strips as it passes through the shielded housing with low resistance.

2. An X-ray inspection system according to claim 1, wherein the inspection station comprises a CT system including the source of X-rays and the detection system.

3. An X-ray inspection system according to claim 2, wherein the CT system performs multi-slice scans of each of the articles when located in the inspection station.

4. An X-ray inspection system according to claim 3, wherein the conveyor system continuously transports articles through the inspection system and the CT system perform multi-slice helical scans.

5. An X-ray inspection system according to claim 1, further including at least one curtain of flexible, X-ray attenuating hanging strips between the inspection station and each of the entrance and exit ports, wherein the hanging strips of each curtain are distributed contiguous with one another substantially in a plane substantially normal to the Z-axis so as to provide uniform attenuation of X-rays emanating from within the inspection station, and allowing articles to displace strips as each article comes in contact with one or more of the hanging strips of the curtain as the article passes through the shielded housing by the conveyor system, wherein the plurality of flexible, X-ray attenuating, spaced-apart, hanging strips are disposed between each of the curtains and the inspection station.

6. An X-ray inspection system according to claim 5, wherein each curtain includes strips of different lengths such that the strips of the curtain that are displaced as an article moves through the curtain by the conveyor assembly is a function of the size of the article.

7. An X-ray inspection system according to claim 6, wherein each curtain includes a plurality of sets of contiguous strips, the strips of each set being of equal length and distributed across the tunnel passageway, and the strips of at least one set are shorter than the strips of at least one other set.

8. An X-ray inspection system for inspecting articles, comprising:

a shielded housing including entrance and exit ports so as to define a tunnel passageway between the entrance and exit ports, and an X-ray inspection station (a) defining a X, Y and Z axis coordinate system, (b) disposed between the entrance and exit ports and (c) including a source of X-rays and a detection system for generating X-ray images of the articles when each is located in the inspection station;

a conveyor assembly for conveying articles to and from the X-ray inspection station through the tunnel passageway along the Z-axis of the coordinate system through the entrance and exit ports; and at least one curtain of flexible, X-ray attenuating strips disposed between the inspection station and each of the entrance and exit ports, wherein the strips are distributed contiguous with one another substantially in a plane substantially normal to the Z-axis so as (a) to provide uniform attenuation of X-rays emanating from within the inspection station, and (b) allow articles to pass through the curtains as they pass through the shielded housing, wherein each curtain includes strips of different lengths such that the strips of the curtain that are displaced as an article moves through the curtain by the conveyor assembly is a function of the size of the article, and wherein each curtain includes a plurality of sets of contiguous strips, the strips of each set being of equal length and distributed across the tunnel passageway, and the strips of at least one set being shorter than the strips of at least one other set.

9. An X-ray inspection system according to claim 8, wherein the set of shorter strips are positioned in front of the set of longer strips and terminate at a higher position than the longer strips so that articles smaller than a predetermined height passing through the curtain will displace the longer strips without displacing the shorter strips.

* * * * *